United States Patent [19]

Park

[11] Patent Number: 4,751,921
[45] Date of Patent: Jun. 21, 1988

[54] BONE CEMENT SYRINGE

[75] Inventor: Joon B. Park, Iowa City, Iowa

[73] Assignee: University of Iowa Research Foundation, Iowa City, Iowa

[21] Appl. No.: 789,782

[22] Filed: Oct. 21, 1985

[51] Int. Cl.$^4$ .............................................. A61F 5/04
[52] U.S. Cl. .................. 128/92 VQ; 604/190
[58] Field of Search .......... 128/92 VQ, 92 VP, 92 V; 604/190, 82, 92, 56

[56] References Cited

U.S. PATENT DOCUMENTS

| | | | |
|---|---|---|---|
| 1,363,128 | 12/1920 | Kitaoka | 604/190 |
| 3,493,503 | 2/1970 | Mass | 604/190 |
| 4,061,143 | 12/1977 | Ishikawa | 604/190 |
| 4,277,184 | 7/1981 | Solomon | 128/92 XO |
| 4,316,462 | 2/1982 | Baker | 604/190 |
| 4,338,925 | 7/1982 | Miller | 128/92 XO |
| 4,405,249 | 9/1983 | Scales | 128/92 G |
| 4,501,135 | 11/1985 | Gorman et al. | 128/92 XO |
| 4,546,767 | 10/1985 | Smith | 128/92 XO |
| 4,576,152 | 3/1986 | Miller et al. | 128/92 XO |

Primary Examiner—C. Fred Rosenbaum
Assistant Examiner—C. W. Shedd
Attorney, Agent, or Firm—Ferris M. Stout

[57] ABSTRACT

A pair of screens in the barrel of a bone cement syringe improves the strength of the bone cement by breaking large bubbles into many small bubbles.

4 Claims, 1 Drawing Sheet

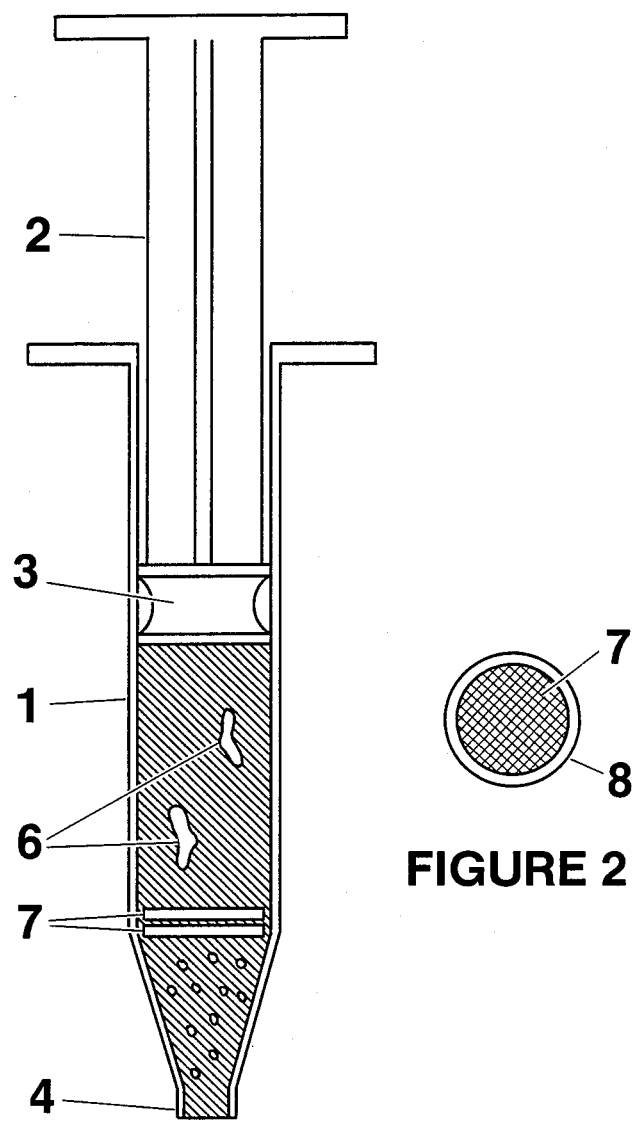

BONE CEMENT SYRINGE

BACKGROUND OF THE INVENTION

1. Field of the Invention

The invention is in the field of coating instruments with material supply; specifically, syringes for expressing bone cement form a self-contained reservoir.

2. Description of the Prior Art

Many prostheses are attached to large bones with a stem, which requires to be cemented into a bone; for example in the case of an artificial hip, into the proximal end of the femur. Since the prosthesis is made of strong materials, the bond of the prosthesis to the bone is the critical point of the installation. It is essential that the bond be as strong and as permanent as possible.

Bone cements are typically polymethylmethacrylate ("PMMA") compositions. A typical proprietary bone cement is Howmedica Radiopaque Simplex P (TM) made and sold by Howmedica Corporation. The cement comes in two components, powder and liquid monomer. The physician mixes the two shortly before use to form a pourable liquid, which is loaded into a syringe made for the purpose. The liquid rapidly thickens into a viscous paste, requiring considerable force for ejection from the syringe. The syringe is put into a hand-held ratchet "gun", whereby the viscous paste can be forced out of the syringe into the bone. U.S. Pat. No. 4,405,249 to Scales ably describes the operation of the syringe and the ratchet gun.

During the operation of mixing the cement components and filling the syringe, bubbles of air are inevitably entrained in the liquid; when the liquid thickens, the bubbles cannot escape from the paste. The bubbles of air are expressed with the cement into the bone; and when the cement hardens, the bubbles leave voids in the solidified cement.

If the voids are larger than a millimeter, they will considerably weaken the cement, and the bond between the prosthesis and the bone into which the prosthesis must be affixed. On the other hand, it has been shown that voids smaller than a millimeter, well distributed in the cement, are beneficial in fatigue tests. The small voids act to limit the propagation of cracks within the cement bond. This is discussed in detail in "Slow Crack Growth in Acrylic Bone Cement", *Journal of Biomedical Materials Research*, 9, 423–439 (1975).

Attempts have been made to remove the bubbles before the cement is used. One such effort involved centrifuging the liquid mixture of components. Though centrifugal forces got rid of bubbles, they also had the effect of classifying solid grains in the solid component of the cement according to size and density, which is unacceptable (see D.W. Burke, E.I. Gates and W.H. Harris, "Improvement of tensile and fatigue properties of PMMA by centrifugation", p. 128, *Transactions* 30th Annual Orthopedic Research Society Meeting, Atlanta, Ga., February 1984.) Unfortunately one cannot apply vacuum to the liquid mixture to remove air bubbles, because the vacuum causes the liquid component of the cement to vaporize, thereby making more voids in the mixture. Vacuum also causes entrained air to expand, and the viscosity of the cement paste captures the expanded bubbles before they can escape.

An alternative approach to the problem of voids is to break the air bubbles up into small bubbles of a size which will not weaken the cement bond, but which will enhance the fatigue properties of the cement. It has been found that this end can be achieved by forcing the cement paste through screens of the proper size in the barrel of the cement syringe.

Filtering screens have been used with injection syringes to screen out impurities in injectable fluids. Exemplary of such devices is U.S. Pat. No. 4,127,131, to Vaillancourt. In this device a filter disk is forced by a retainer ring into a recess in a hub which attaches to the nipple of the syringe. This arrangement, and others like it in which filtration occurs after the fluid in the syringe has passed through the nipple of the syringe, will not serve for the purpose of this invention. The small area of the filter would offer such great resistance to the viscous paste of the bone cement, that the force required would probably rupture the filter. Moreover, a bubble in the nipple of the syringe would be dispersed only in the small volume of cement contained within the nipple, whereas what is sought is as great a dispersion of microbubbles as is possible.

What is needed therefore is filtering means within the barrel of the cement syringe, of large enough mesh to pass the largest particles in the solid component of the cement paste, yet small enough to form microbubbles and disperse them among a quantity of the cement.

BRIEF DESCRIPTION OF THE DRAWINGS

FIG. 1 is a cross-section through a bone cement syringe with screens in place.

FIG. 2 is a plan view of a screen.

DESCRIPTION OF A PREFERRED EMBODIMENT

A preferred embodiment of the invention is shown in the drawings.

FIG. 1 of the drawing shows a cross-sectional view of a typical loaded cement syringe, its barrel 1 enclosing a piston 2 to which is attached plunger 3. At the end of the syringe nipple 4 is adapted for attachment to a large-bore needle (not shown). A bubble of air is schematically represented at 6.

In the bottom of the barrel of the syringe two screens 7 are shown. The screens are mounted in and supported by rims 8. The outside diameter of the screen ribs allow a sliding fit with the inside diameter of the syringe barrel. FIG. 2 is a plan view of one of the screens and its supporting rim.

Returning to FIG. 1, bone cement is shown below the screens as though some of it were expressed through the screens. Microbubbles of air are represented at 9, showing how a larger bubble has been disrupted in its passage through the screens.

In this preferred embodiment dual screens are used. In another embodiment a single screen is used; but while an increase in strength is achieved with the single screen, it is considerably less than the increase in strength provided by dual screens. In yet other embodiments, more than two screens are used, which are effective in increasing strength of the cement, but require more force to express the cement paste through the screens.

The apertures of the screens must be fine enough to break up air bubbles into microbubbles, but not so fine that the coarser particles of the solid component of the cement paste cannot pass through them. For bone cements presently available, we have found that the apertures may be as fine as 100 microns, or as coarse as 300 microns. In this preferred embodiment an 80 mesh screen is used with an aperture of 100 microns.

The description of this preferred embodiment is only illustrative of the invention; it is not to be construed as limiting the scope of the invention, which is as defined in the claims.

What is claimed is:

1. In a syringe of the type used for injecting bone cement paste in surgical procedures, the syringe having an open end for receiving a plunger, a barrel of constant cross-section, and an end beyond the barrel of decreasing cross section through which the cement paste is expressed, means for improving the ultimate strength of bone cement by breaking up large bubbles in the bone cement paste into small bubbles, the means comprising at least one screen located in the barrel of the syringe at the point of decreasing cross section.

2. The bone cement syringe of claim 1 wherein the mesh of said at least one screen is between 50 and 100 mesh.

3. Means for improving the strength of bone cement used in surgical procedures, the means comprising at least one screen located in that part of a bone cement syringe barrel which has a constant cross sectional area and which is beyond the farthest incursion of a syringe plunger fitted to the barrel, whereby bubbles in the bone cement paste are broken up into smaller bubbles as the bone cement paste is expressed through the screens by motion of the plunger.

4. A method for improving the strength of bone cement by reducing the size of bubbles in bone cement paste, the method comprising the steps of loading the bone cement paste into a syringe in which screens have been provided at the point of extreme incursion of the syringe's plunger; and breaking up bubbles in said loaded bone cement paste into microbubbles in the expressed bone cement paste by applying pressure to and thereby moving the syringe plunger and forcing the bone cement paste through the screens which break up and distribute the large air bubbles as microbubbles; the weakening effect of large bubbles thereby being avoided in the cured bone cement.

* * * * *